United States Patent [19]
Abe

[11] Patent Number: 6,066,127
[45] Date of Patent: May 23, 2000

[54] LASER TREATMENT APPARATUS

[75] Inventor: Hitoshi Abe, Aichi, Japan

[73] Assignee: Nidek Co., Ltd., Aichi, Japan

[21] Appl. No.: 09/157,314

[22] Filed: Sep. 21, 1998

[30] Foreign Application Priority Data

Sep. 30, 1997 [JP] Japan .................................. 9-284680

[51] Int. Cl.$^7$ .................................................. A61B 18/18
[52] U.S. Cl. .................................. 606/2; 606/10; 606/11
[58] Field of Search .................................. 606/2, 3, 9, 10, 606/11, 12, 14, 15, 16, 17, 19; 372/92, 98, 97, 99, 107; 359/872

[56] References Cited

U.S. PATENT DOCUMENTS

| 5,172,264 | 12/1992 | Morrow ................................ 606/11 X |
| 5,180,378 | 1/1993 | Kung et al. ............................... 606/10 |
| 5,254,112 | 10/1993 | Sinofsky et al. ........................... 606/10 |
| 5,387,211 | 2/1995 | Saadatmanesh et al. .................. 606/10 |
| 5,540,676 | 7/1996 | Freiberg .................................... 606/3 |
| 5,634,922 | 6/1997 | Hirano et al. ............................. 606/10 |
| 5,662,644 | 9/1997 | Swor ........................................ 606/9 |
| 5,746,735 | 5/1998 | Furumoto et al. ....................... 606/10 |
| 5,759,200 | 6/1998 | Azar ...................................... 606/11 X |
| 5,785,703 | 7/1998 | Goodman et al. ....................... 606/10 |
| 5,873,875 | 2/1999 | Altshuler ................................. 606/10 |

FOREIGN PATENT DOCUMENTS

| 8-229064 | 9/1996 | Japan ............................. A61F 9/007 |
| 9-38101 | 2/1997 | Japan ............................. A61B 17/36 |
| 9-192140 | 7/1997 | Japan ............................. A61B 17/36 |

Primary Examiner—Linda C. M. Dvorak
Assistant Examiner—Sonya Harris-Ogugua
Attorney, Agent, or Firm—Sughrue, Mion, Zinn, Macpeak & Seas, PLLC

[57] ABSTRACT

A laser treatment apparatus which performs a medical or surgical treatment using laser-beam irradiation, The apparatus has a solid-state laser medium for obtaining a laser beam and an excitation light source for exciting the solid-state laser medium. The apparatus further has a first optical system having a Q-switch which emits light oscillated by the solid-state laser medium as a pulse wave laser beam, and a second optical system which emits the light oscillated by the solid-state laser medium as a continuous wave laser beam. An optical path for the light oscillated by the solid-state laser medium is switched to one of optical paths of the first and second optical systems. With this apparatus, plural oscillation modes and wavelengths can be switched over in accordance with the treatment object, and the load on the user is reduced.

9 Claims, 3 Drawing Sheets

LASER TREATMENT APPARATUS

BACKGROUND OF THE INVENTION

The present invention relates to a laser treatment apparatus which performs a treatment by irradiating a part to be treated (diseased part) of the patient with a laser beam.

Laser treatment apparatuses are known, which perform treatments by irradiating parts to be treated (diseased parts) of the patients with laser beams. These apparatuses are selectively used in accordance with various treatment objects.

For example, the treatment effect of laser irradiation in the CW (Continuous Wave) mode is mainly based on the thermal function. A laser knife which utilizes incision on the basis of gasification or vaporization of the tissue due to heat is used in fields such as the surgery. In the field of the ophthalmology, a laser apparatus which is smaller in output power than a laser knife is used in a photocoagulation treatment of a diseased part and the periphery of the part, against a disease in an eyeground, such as maculopathy or retinal detachment.

On the other hand, in the treatment effect of laser irradiation in the pulse wave mode, the destruction function by a high energy is greater in degree than the thermal function. Such laser irradiation is used in a treatment based on tissue destruction of a diseased part. In the field of the ophthalmology, such laser irradiation is used in a treatment of secondary cataract occurring in a posterior capsule of lens, or in that of glaucoma based on perforation or incision of the iris or the angle.

However, the difference in the effect on the living body is not caused only by the above-mentioned difference in the oscillation mode. Parameters such-as the wavelength of the laser beam, the output power, and the irradiation time must be optimumly selected in accordance with the treatment object. In order to cope with various treatments, therefore, it is required to provide plural laser treatment apparatuses which respectively correspond to various treatment objects. This requires the load on the user, such as the increased cost of purchase, the need of securing the installation location, etc.

SUMMARY OF THE INVENTION

In view of the above-discussed problem, it is an object of the invention to provide a laser treatment apparatus in which plural oscillation modes and wavelengths can be switched over in accordance with the treatment object, thereby reducing the load on the user.

In order to solve the problems, the invention is characterized by the following configuration.

(1) A laser treatment apparatus for performing a medical or surgical treatment using laser-beam irradiation, the apparatus comprising:

a solid-state laser medium for obtaining a laser beam;

an excitation light source which excites the solid-state laser medium;

a first optical system having a Q-switch, which emits light oscillated by the solid-state laser medium as a pulse wave laser beam;

a second optical system which emits the light oscillated by the solid-state laser medium as a continuous wave laser beam; and an optical-path switching system, which switches an optical path for the light oscillated by the solid-state laser medium to one of optical paths of the first and second optical systems.

(2) A laser treatment apparatus according to (1), wherein at least one of the first and second optical systems has wavelength converting system which converts a wavelength of the light oscillated by the solid-state laser medium.

(3) A laser treatment apparatus according to (2), wherein the wavelength converting system converts light of a fundamental wavelength oscillated by the solid-state laser medium, into a second harmonic.

(4) A laser treatment apparatus according to (1), further comprising:

a controller, which controls an exciting operation of the excitation light source based on a switching signal of the optical-path switching system.

(5) A laser treatment apparatus according to (1), wherein the solid-state laser medium is a solid-state laser medium that is doped with Nd and that is represented by an Nd:YAG rod.

(6) A laser treatment apparatus according to (1), wherein the Q-switch includes a dye cell of a saturable absorber.

(7) A laser treatment apparatus according to (1), wherein the second optical system includes a nonlinear optical crystal.

(8) A laser treatment apparatus according to (7), wherein the nonlinear optical crystal is one of a KTP crystal, a BBO crystal, and an LBO crystal.

(9) A laser treatment apparatus according to (1), wherein the optical-system switching system includes a movable mirror.

The present disclosure relates to the subject matter contained in Japanese patent application No. Hei. 9-284680 (filed on Sep. 30, 1997) which is expressly incorporated herein by reference in its entirety.

DETAILED DESCRIPTION OF THE PREFERRED EMBODIMENT

Figure 1:
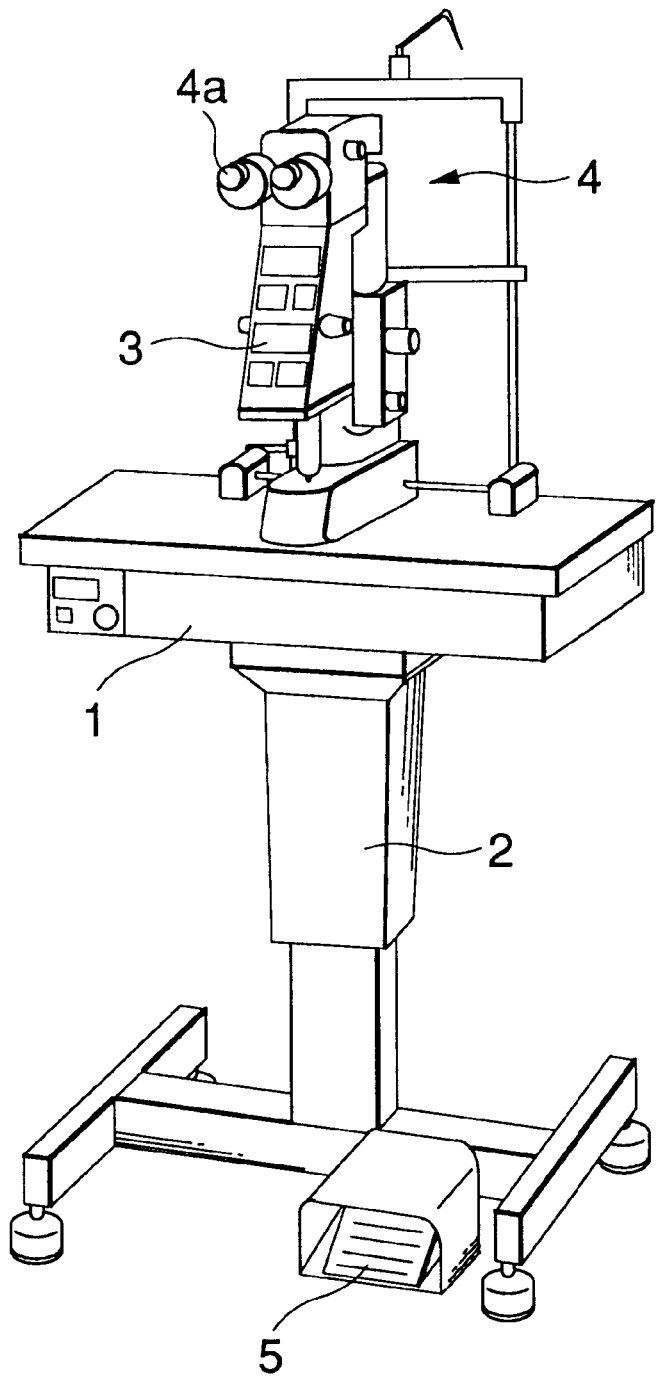
FIG. 1 is an external diagrammatic view of a laser treatment apparatus which is an embodiment.

Hereinafter, the invention will be described by illustrating an embodiment with reference to the accompanying drawings. FIG. 1 is an external diagrammatic view of a laser treatment apparatus.

The reference numeral 1 designates the body of the apparatus which houses a treatment laser source, a light guiding optical system, etc. The reference numeral 2 designates a pedestal which is vertically movable and to which the apparatus body 1 is fixed. The reference numeral 3 designates a control panel through which conditions of the laser irradiation are set, 4 designates a slit lamp delivery device which irradiates a diseased part of a patient's eye with the laser beam while observing the patient's eye, and 5 designates a foot switch which outputs a trigger signal for laser irradiation. In the embodiment, a laser beam is guided from the apparatus body 1 to an irradiation optical system (not shown) of the slit lamp delivery device 4, by mirrors which are not shown.

Figure 2:
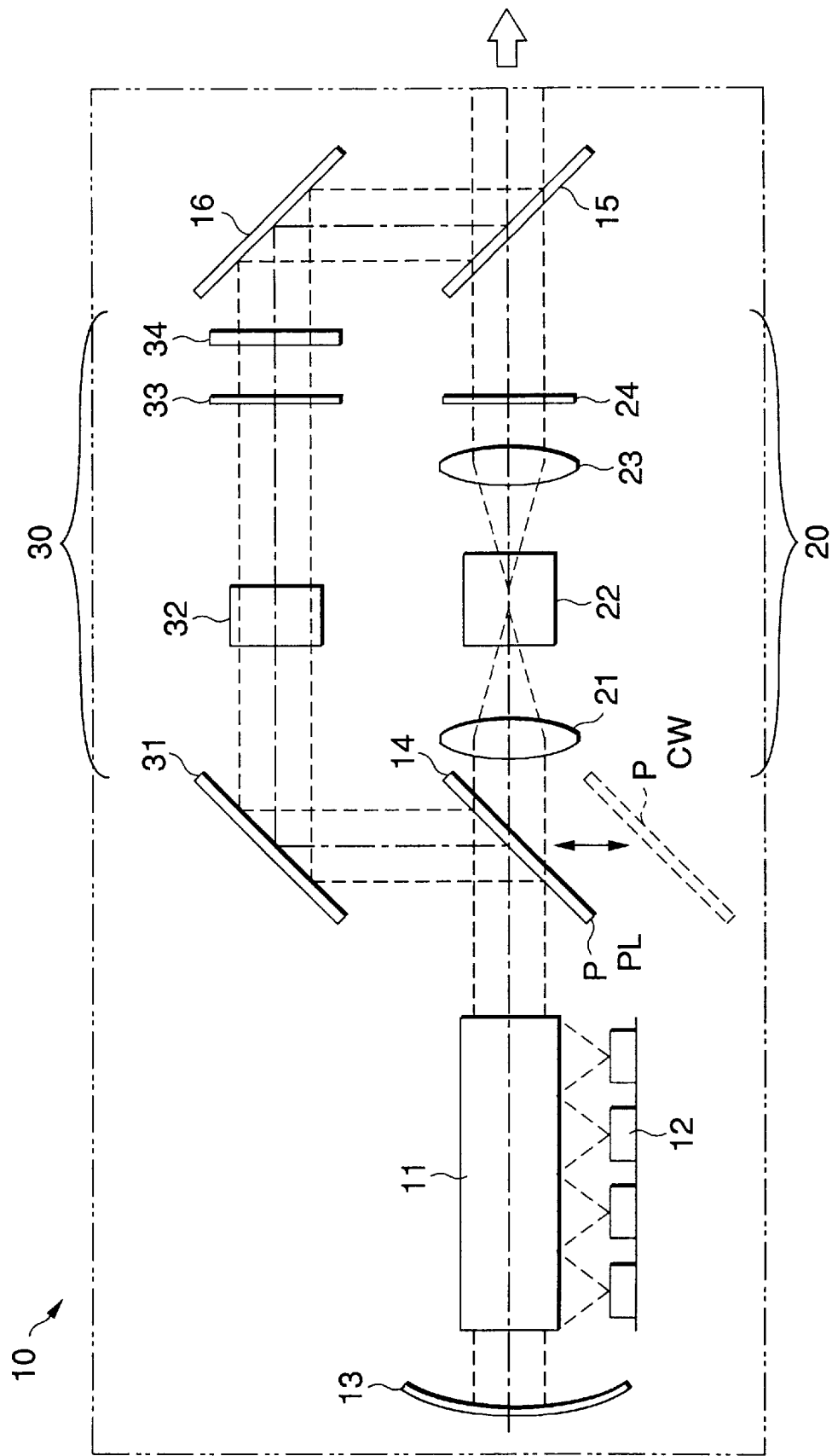
FIG. 2 is a diagram of main portions of a laser source.

FIG. 2 is a diagram of main portions of the treatment laser source 10 disposed in the apparatus body 1. The reference numeral 11 designates a solid-state laser rod, 12 designates an excitation light source, 13 designates an end mirror, 14 designates a driven mirror, 15 designates a dichroic mirror, 16 designates a mirror, 20 designates a CW optical system, and 30 designates a pulse wave optical system. In the embodiment, an Nd:YAG rod which oscillates light of the fundamental wavelength of 1,064 nm is used as the solid-state laser rod 11, and a semiconductor laser source is used as the excitation light-source 12. The end mirror 13 is a total reflection mirror. The dichroic mirror 15 has properties in which light of Nd:YAG of the fundamental wavelength of 1,064 nm is reflected, and light of the second harmonic of 532 nm is allowed to pass therethrough.

The CW optical system 20 includes a condenser lens 21, a nonlinear optical crystal 22, a collimator lens 23, and an output mirror 24. As the nonlinear optical crystal 22, a KTP crystal, a BBO crystal, an LBO crystal, or the like is used in order to convert 1,064 nm which is the fundamental wavelength of Nd:YAG into 532 nm which is the second harmonic. The output mirror 24 has properties in which light of the fundamental wavelength of 1,064 nm is reflected, only several percent of light of the second harmonic of 532 nm is allowed to pass therethrough, and the remainder of the light of the second harmonic is reflected.

The pulse wave optical system 30 includes a mirror 31, a Q-switch 32, an output mirror 33, and a polarizing plate 34. With the aid of the Q-switch 32, a giant pulse, which has a narrow pulse width and a high peak output, can be obtained for a short time. In the embodiment, a dye cell which is a saturable absorber is used as the Q-switch. A dye cell has properties in which, during a normal state, light is not allowed to transmit therethrough and, when the light intensity of the laser medium reaches a specified value, the cell becomes transparent. The polarizing plate 34 has a function of attenuating the output power of the oscillated laser beam to a preset laser output power, and is controlled by a control unit 40 which will be described later.

Figure 3:
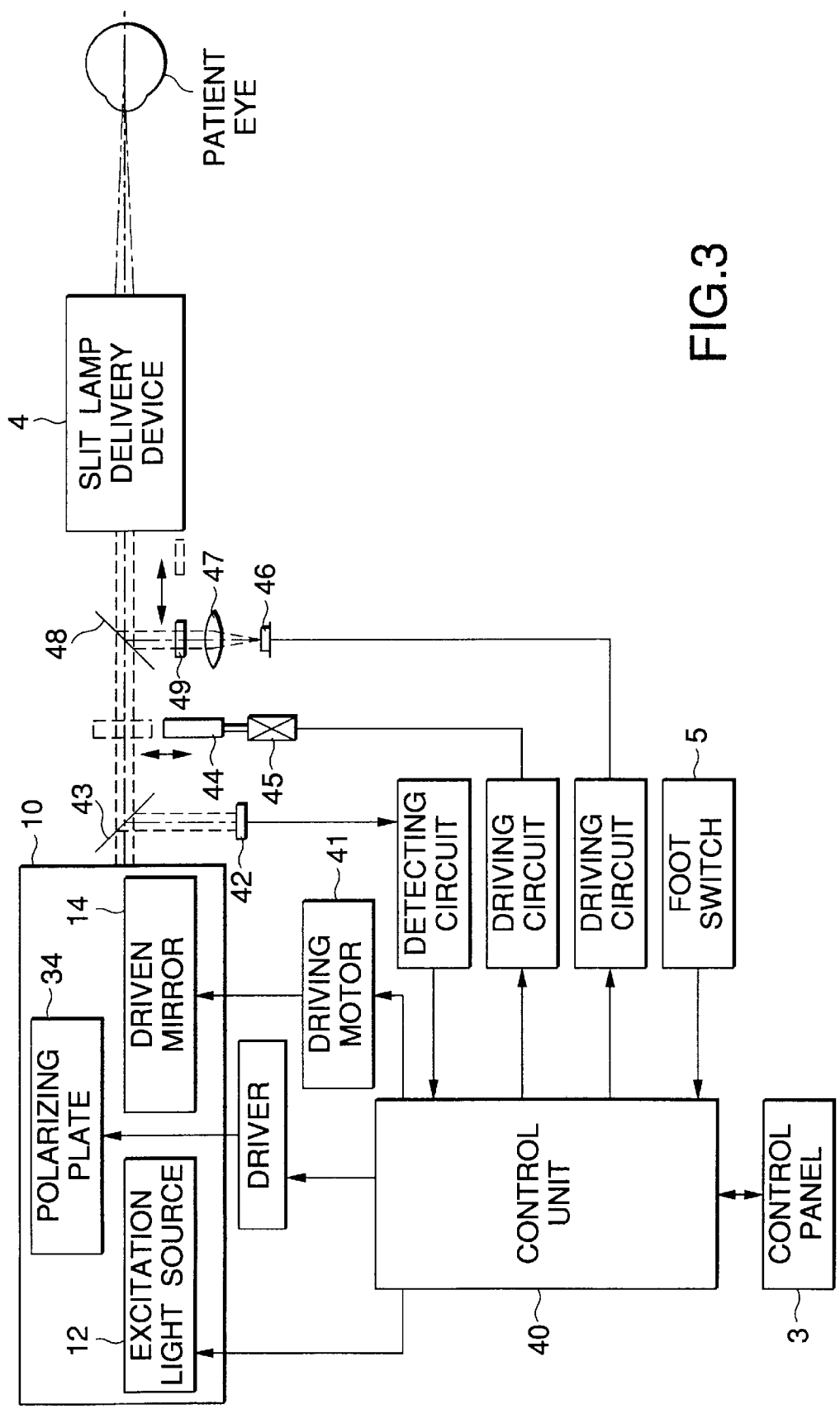
FIG. 3 is a diagram of main portions of a control system and an optical system of the laser treatment apparatus.

The laser treatment apparatus which has the above-described configuration will be described with reference to FIG. 3 which is a diagram showing main portions of the control and optical systems, in the cases of (I) the CW mode and (II) the pulse wave mode.

(I) In the Case of the CW Mode

When a photocoagulation treatment such as a treatment of a disease in an eyeground, for example, maculopathy or retinal detachment is to be performed, the operator operates the control panel 3 to select the CW mode and sets coagulation conditions such as the laser output power and the coagulation time. In the case of the CW mode, the control unit 40 supplies a power to the excitation light source 12 so as to continuously excite the laser rod 11, and controls the driving of a driving motor 41 so as to locate the driven mirror 14 at the position of the broken line $P_{CW}$.

The light of the fundamental wavelength of 1,064 nm, which is emitted from the laser rod 11 excited by the excitation light source 12, is condensed in energy density by the condenser lens 21, and then enters the nonlinear optical crystal 22. The light of the fundamental wavelength which enters the nonlinear optical crystal 22 is partially converted into the second harmonic when the light passes through the nonlinear optical crystal 22. The light of the fundamental wavelength and that of the second harmonic which have passed through the nonlinear optical crystal 22 are converted into parallel beams by the collimator lens 23. Thereafter, most of the light is reflected by the output mirror 24 and only part of the light of the second harmonic is transmitted therethrough. The reflected light is amplified with being repeatedly reflected between the end mirror 13 and the output mirror 24. The light of the second harmonic which is transmitted through the output mirror 24 is used as treatment light for a photocoagulation treatment. The laser light which has passed through the dichroic mirror 15 and emitted from the laser source 10 is partly reflected by a beam splitter 43 to be detected by a light receiving device 42. The control unit 40 adjusts the output of the excitation light source 12 on the basis of a detection signal of the light receiving device 42 and the preset coagulation conditions, thereby stabilizing the laser output.

While observing the patient's eye through an observation optical system 4a of the slit lamp delivery device 4, the operator operates a joy stick or the like so that an aiming beam emitted from an aiming light source 46 is aimed at the diseased part so as to perform an alignment operation, and adjusts the spot size and the like. In the embodiment, a semiconductor laser is used as the aiming light source 46, and the aiming beam emitted from the aiming light source 46 is converted into parallel beams by a collimator lens 47 and then set to be coaxial with the treatment laser beam by a dichroic mirror 48. The beams are guided into the irradiation optical system of the slit lamp delivery device 4. The dichroic mirror 48 has properties in which the aiming beam is reflected and the treatment laser beam is transmitted therethrough.

When the alignment operation using the aiming beam is completed, the operator presses the foot switch 5 to send the trigger signal. Upon reception of the trigger signal, the control unit 40 controls the driving of a solenoid 45 so as to retract a safety shutter 44 from the laser beam axis. When the safety shutter 44 is retracted, the treatment beam of the second harmonic of 532 nm is irradiated on the patient's eye through the irradiation optical system of the slit lamp delivery device 4, and a photocoagulation treatment is performed.

When the preset coagulation time elapses, the control unit 40 drives the solenoid 45 so as to insert the safety shutter 44 into the laser beam axis, thereby interrupting the laser beam. Even before the preset coagulation time elapses, the operator may return the foot switch 5 to cancel the trigger signal, so that the control unit 40 inserts the safety shutter 44 into the laser beam axis to interrupt the laser beam.

(II) In the Case of the Pulse Wave Mode

When a treatment such as a treatment of secondary cataract, or that of glaucoma based on perforation of the iris or the angle, the operator operates the control panel 3 to select the pulse wave mode and sets irradiation conditions such as the laser output power and the number of irradiation pulses.

When the pulse wave mode is set, the control unit 40 controls the driving of the driving motor 41 so as to locate the driven mirror 14 at the position of the solid line $P_{PL}$, and stops the power supply to the excitation light source 12, thereby temporarily suspending the excitation of the laser rod 11.

While observing the patient's eye through the observation optical system 4a of the slit lamp delivery device 4, the operator performs the alignment operation so that the aiming beam emitted from the aiming light source 46 is aimed at the diseased part. In the case of the pulse wave mode, the control unit 40 controls an aperture 49 having two holes to be inserted into the aiming beam axis, thereby splitting the aiming beam flux into two beams. An intersection of the two aiming beams corresponds to the focal position of the treatment laser beam. The operator performs the alignment operation by setting the intersection to coincide with the diseased part.

When the alignment operation using the aiming beams is completed, the operator presses the foot switch 5 to send the trigger signal. Upon reception of the trigger signal, the control unit 40 controls the driving of the solenoid 45 so as to retract the safety shutter 44 from the laser beam axis, and supplies a power to the excitation light source 12, thereby exciting the laser rod 11. Even when the laser rod 11 is excited, a resonator constituted by the end mirror 13 and the output mirror 33 is not formed because the Q-switch 32 interrupts the beam, and the distribution of inverted population is increased without starting the laser oscillation.

When the distribution of inverted population is increased and the light intensity reaches the specified value, the dye cell which is the Q-switch 32 becomes transparent so that light can be transmitted therethrough. Therefore, the laser oscillation is rapidly started and a laser beam having a high peak output is emitted, for a short time. The emitted laser beam is subjected to the power control by the polarizing plate 34, reflected by the mirror 16 and the dichroic mirror 15, and then directed to the slit lamp delivery device 4.

After emitted from the laser source 10, the laser beam is irradiated on the patient's eye through the irradiation optical system of the slit lamp delivery device 4. In the diseased part, nuclear destruction due to generation of a plasma occurs, whereby the treatment is performed.

The control unit 40 controls the excitation light source 12 on the basis of the preset number of irradiation pulses so as to emit the preset number of irradiation pulses. When the irradiation for the preset pulse number is completed, the control unit 40 drives the solenoid 45 so as to insert the safety shutter 44 into the laser beam axis.

As described above, in accordance with the treatment object, the CW mode and the pulse wave mode, and the fundamental wave and the second harmonic can be selectively used. Therefore, even a single apparatus can cope with different kinds of treatments, and the loads on the user such as the cost of purchase and the installation location can be hence reduced.

The oscillation mode and the wavelength which are optimum to the treatment object are selected by switching over the optical systems in the laser source with respect to the single laser rod. Consequently, the oscillation efficiency is excellent, and the reduction of the running cost and the production cost is enabled.

In the embodiment, the laser oscillation mode is switched over by inserting or retracting the driven mirror 14 into or from the laser oscillation axis. Alternatively, the CW oscillation optical system and the pulse wave oscillation optical system may be inserted into or retracted from the oscillation axis by a sliding mechanism or a rotating mechanism.

In the pulse oscillation mode, the pulse oscillation is not restricted to a giant pulse or repetitive pulses due to the Q-switch, and the pulse oscillation due to the mode-locking is enabled. As the Q-switch, various kinds of known Q-switches other than a saturable absorber may be used.

In the above, the embodiment which uses side pumping due to the semiconductor laser has been described. Alternatively, end pumping in which excitation is conducted in the axial direction of the laser medium may be used, or a flash lamp or an arc lamp may be used.

As described above, according to the invention, plural laser beams of different kinds can be obtained from a single treatment laser source, and hence a single apparatus can perform plural kinds of treatments in accordance with the treatment object. Furthermore, the loads on the user such as the cost of purchase and the installation location can be reduced, and the running cost and the production cost can be lowered.

What is claimed is:

1. A laser treatment apparatus for performing a medical or surgical treatment using laser-beam irradiation, said apparatus comprising:

a solid-state laser medium for obtaining a laser beam;

an excitation light source which excites said solid-state laser medium;

a first optical system having a Q-switch, which emits light oscillated by said solid-state laser medium as a pulse wave laser beam;

a second optical system which emits the light oscillated by said solid-state laser medium as a continuous wave laser beam; and an optical-path switching system, which switches an optical path for the light oscillated by said solid-state laser medium to one of optical paths of said first and second optical systems.

2. A laser treatment apparatus according to claim 1, wherein at least one of said first and second optical systems has wavelength converting system which converts a wavelength of the light oscillated by said solid-state laser medium.

3. A laser treatment apparatus according to claim 2, wherein said wavelength converting system converts light of a fundamental wavelength oscillated by said solid-state laser medium, into a second harmonic.

4. A laser treatment apparatus according to claim 1, further comprising:

a controller, which controls an exciting operation of said excitation light source based on a switching signal of said optical-path switching system.

5. A laser treatment apparatus according to claim 1, wherein said solid-state laser medium is a solid-state laser medium that is doped with Nd and that is represented by an Nd:YAG rod.

6. A laser treatment apparatus according to claim 1, wherein said Q-switch includes a dye cell of a saturable absorber.

7. A laser treatment apparatus according to claim 1, wherein said second optical system includes a nonlinear optical crystal.

8. A laser treatment apparatus according to claim 7, wherein said nonlinear optical crystal is one of a KTP crystal, a BBO crystal, and an LBO crystal.

9. A laser treatment apparatus according to claim 1, wherein said optical-system switching system includes a movable mirror.

* * * * *